(12) United States Patent
Jaiswal et al.

(10) Patent No.: US 11,056,231 B2
(45) Date of Patent: Jul. 6, 2021

(54) UTILIZING IOT DEVICES FOR DETECTING AN EMERGENCY AND LOCATING A CONVENIENT PARKING SPACE

(71) Applicant: International Business Machines Corporation, Armonk, NY (US)

(72) Inventors: Peeyush Jaiswal, Boca Raton, FL (US); Priyansh Jaiswal, Boca Raton, FL (US); Burt L. Vialpando, Irving, TX (US); Paul Llamas Virgen, Jalisco (MX); Annita Tomko, Jalisco (MX); David Jaramillo, Durham, NC (US)

(73) Assignee: International Business Machines Corporation, Armonk, NY (US)

( * ) Notice: Subject to any disclaimer, the term of this patent is extended or adjusted under 35 U.S.C. 154(b) by 281 days.

(21) Appl. No.: 15/810,351

(22) Filed: Nov. 13, 2017

(65) Prior Publication Data

US 2019/0147138 A1 May 16, 2019

(51) Int. Cl.
*G16H 40/20* (2018.01)
*G16H 50/30* (2018.01)
*G16H 50/20* (2018.01)

(52) U.S. Cl.
CPC ............. *G16H 40/20* (2018.01); *G16H 50/20* (2018.01); *G16H 50/30* (2018.01)

(58) Field of Classification Search
CPC ...... G16H 50/30; G16H 40/20; B60R 25/806; B60T 2201/10; E04H 6/00; E04H 6/426; G06K 9/00812; G06Q 2240/00; G08G 1/14
See application file for complete search history.

(56) References Cited

U.S. PATENT DOCUMENTS

| | | | |
|---|---|---|---|
| 8,018,329 B2 | 9/2011 | Morgan et al. | |
| 8,581,712 B2 | 11/2013 | Morgan et al. | |
| 9,123,058 B2 | 9/2015 | Ricci | |
| 9,594,956 B2* | 3/2017 | Cohen | G07B 15/02 |
| 9,775,520 B2* | 10/2017 | Tran | A61B 5/1116 |
| 10,207,041 B2* | 2/2019 | Soykan | A61B 5/145 |
| 2010/0148947 A1 | 6/2010 | Morgan et al. | |
| 2012/0056758 A1* | 3/2012 | Kuhlman | G08G 1/14 340/932.2 |

(Continued)

FOREIGN PATENT DOCUMENTS

| | | | | |
|---|---|---|---|---|
| GB | 2546143 B | * | 4/2020 | G08G 1/143 |
| WO | 2011090997 A1 | | 7/2011 | |

OTHER PUBLICATIONS

Siemens Smart City Vision, available at https://web.archive.org/web/20170803113056/http://www.mobility.siemens.com/mobility/global/en/urban-mobility/road-solutions/integrated-smart-parking-solution/Pages/integrated-smart-parking-solution.aspx (Aug. 3, 2017) (Year: 2017).*

(Continued)

*Primary Examiner* — Evangeline Barr
*Assistant Examiner* — Jordan L Jackson
(74) *Attorney, Agent, or Firm* — Joseph P. Curcuru; Gilbert Harmon, Jr.

(57) ABSTRACT

Embodiments describe an approach to monitoring user health data. Determining if the user is having an emergency based on the user health data. Responsive to determining the user is having an emergency the user's location. Identifying one or more available parking spaces based on the user's location, and outputting locations of one or more available parking spaces to the user.

20 Claims, 3 Drawing Sheets

(56) References Cited

U.S. PATENT DOCUMENTS

| | | |
|---|---|---|
| 2013/0135118 A1 | 5/2013 | Ricci |
| 2015/0138362 A1 | 5/2015 | Stefik et al. |
| 2015/0334545 A1 | 11/2015 | Maier et al. |
| 2016/0330770 A1 | 11/2016 | Lee et al. |

OTHER PUBLICATIONS

Streetline Inc., available at https://www.youtube.com/user/streetlineparking/videos? (Year: 2011).*
Lauryn Chamberlin, GeoMarketing 101: What Is Geofencing?, Geomarketing From Yext (Mar. 7, 2016) (Year: 2016).*
Solving Tough Parking Management Challenges Using Technology, Data, and IOT, All Traffic Solutions (Aug. 15, 2017) (Year: 2017).*
Baker, Sweating Rate and Sweat Sodium Concentration in Athletes: A Review of Methodology and Intra/Interindividual Variability, 47 (Sup 1) Sports Med S111-S128 (Mar. 22, 2017)[ (Year: 2017).*
Hee Chan Kim et al, A Wrist-Worn Integrated Health Monitoring Instrument with a Tele-Reporting Device for Telemedicine and Telecare, 55(5) IEEE Transactions on Instrumentation and Measurement 1655-1661(Nov. 2006) (Year: 2006).*
Benton, Ben, "Tennessee tests smart parking lots with real-time parking space information", Times Free Press, <http://www.timesfreepress.com/news/local/story/2015/feb/03/parking-sites-project-helps-truckers-find-tim/286144/>, Feb. 3, 2015, 4 pages.
Gandhi et al., "A Prototype for IoT based Car Parking Management System for Smart Cities", Indian Journal of Science and Technology, vol. 9(17), DOI: 10.17485/ijst/2016/v9i17/92973, May 2016, 6 pages.

\* cited by examiner

UTILIZING IOT DEVICES FOR DETECTING AN EMERGENCY AND LOCATING A CONVENIENT PARKING SPACE

BACKGROUND OF THE INVENTION

The present invention relates generally to the field of patient health, and more particularly to utilize smart devices to locate emergency parking.

Every parking lot or parking structure has a set of preferred parking spaces. Some spots are government regulated, as in the case of handicap parking, while others are dictated by a variety of business functionality, as in reserved spots for company very important person(s) (V.I.P's), doctors, Executive member's etc. But the remainder of the parking spaces are taken on a first-come, first-served basis by everyone else. Additionally, there are instances where the reserved and/or government regulated spaces are completely empty and the rest of the parking structure is full. In most emergency settings time is crucial. Finding a parking location at a hospital or emergency center can be time consuming.

SUMMARY

Embodiments of the present invention disclose a method, a computer program product, and a system for detecting a health emergency and assigning preferred parking, the method can include monitoring, by one or more processors, user health data. Determining, by the one or more processors, if the user is having an emergency based on the user health data. Responsive to determining the user is having an emergency, identifying, by the one or more processors, the user's location. Identifying, by the one or more processors, one or more available parking spaces based on the user's location, and outputting, by the one or more processors, locations of one or more available parking spaces to the user.

According to an embodiment of the present invention, a computer program product for detecting a health emergency and assigning preferred parking, the computer program product comprising: one or more computer readable storage devices and program instructions stored on the one or more computer readable storage devices, the stored program instructions can include program instructions to monitor user health data. Program instructions to determine if the user is having an emergency based on the user health data. Responsive to determining the user is having an emergency, program instructions to identify the user's location. Program instructions to identify one or more available parking spaces based on the user's location, and program instructions to output locations of the one or more available parking spaces to the user.

According to another embodiment of the present invention, a computer system for detecting a health emergency and assigning preferred parking, the computer system can include: one or more computer processors, one or more computer readable storage devices, program instructions stored on the one or more computer readable storage devices for execution by at least one of the one or more computer processors, the stored program instructions can include program instructions to monitor user health data. Program instructions to determine if the user is having an emergency based on the user health data. Responsive to determining the user is having an emergency, program instructions to identify the user's location. Program instructions to identify one or more available parking spaces based on the user's location, and program instructions to output locations of the one or more available parking spaces to the user.

DETAILED DESCRIPTION

Embodiments of the present invention can assign available parking spaces on a temporary basis (similar to handicapped parking) and/or preferred but based on the needs of the occupants of the vehicle. While handicapped parking requires a government assigned handicapped parking sticker or placard on the vehicle itself, embodiments of the present invention rely on an Internet of Things (IOT) health-monitoring device that can emit personal data for the occupant in the vehicle. Embodiments of the present invention can monitor a user's diagnostics and determine if the user is having an emergency or is in a temporary handicapped state, such as a pregnancy, an injury, is intoxicated, is having a heart attack, etc., and assign a preferred and/or most convenient and available parking space automatically, in which improves the art of emergency care and parking assignments and solves the issue of having unoccupied preferred and/or priority parking.

It should be known that the terms parking space and preferred parking space are interchangeable and/or can contain the same meaning.

Figure 1:
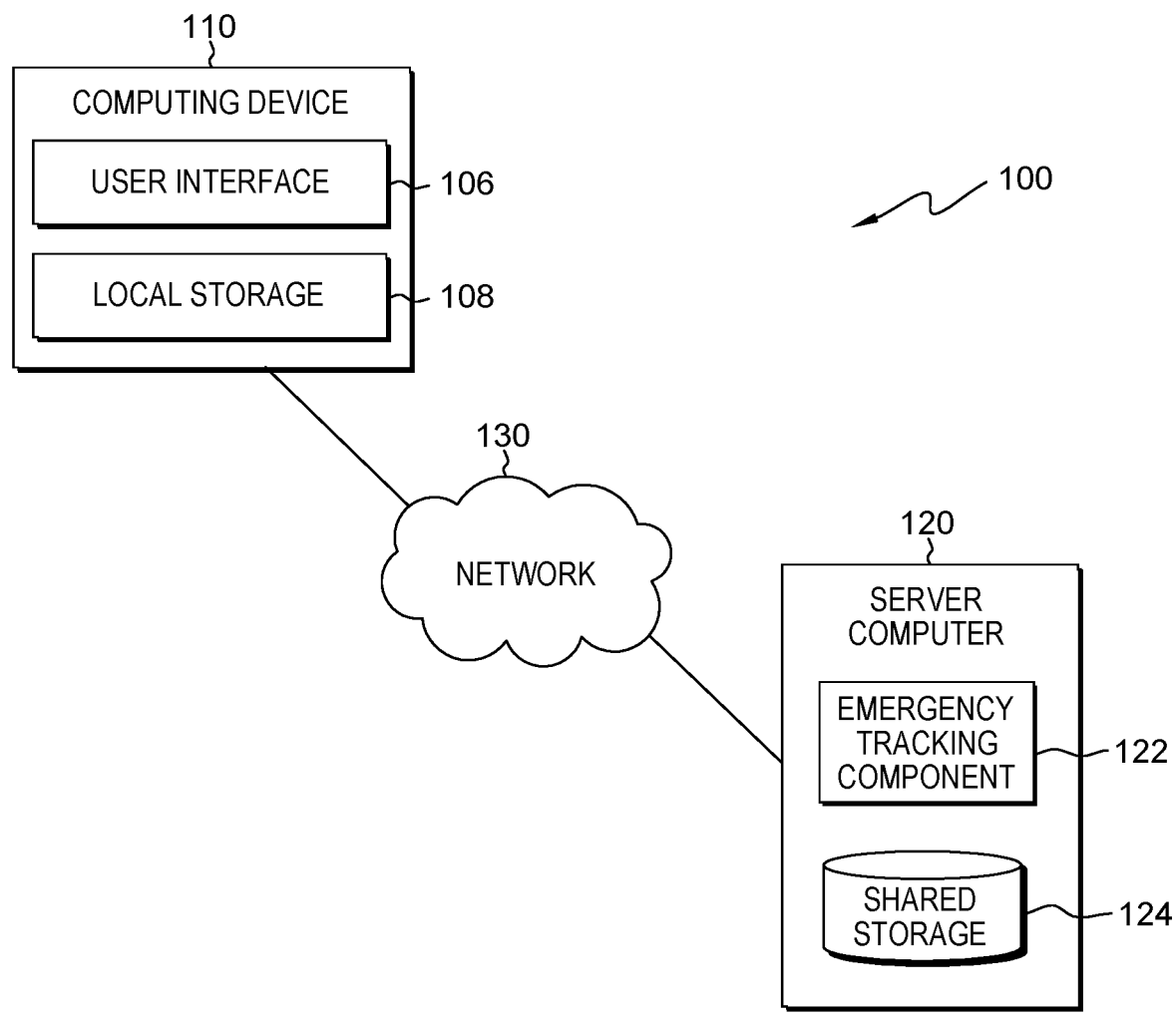
FIG. 1 is a functional block diagram illustrating a distributed data processing environment, in accordance with an embodiment of the present invention.

FIG. 1 is a functional block diagram illustrating a distributed data processing environment, generally designated 100, in accordance with one embodiment of the present invention. The term "distributed" as used in this specification describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes mobile device 110, server computer 120, interconnected over network 130. Network 130 can be, for example, a telecommunications network, a local area network (LAN), a wide area network (WAN), such as the Internet, or a combination of the three, and can include wired, wireless, or fiber optic connections. Network 130 can include one or more wired and/or wireless networks that are capable of receiving and transmitting data, voice, and/or video signals, including multimedia signals that include voice, data, and video information. In general, network 130 can be any combination of connections and protocols that will support communications between mobile device 110 and server computer 120, and other computing devices (not shown in FIG. 1) within distributed data processing environment 100.

In various embodiments, computing device 110 can be, but is not limited to, a wearable fitness device, a standalone device, a server, a laptop computer, a tablet computer, a netbook computer, a personal computer (PC), a smart phone, a desktop computer, a smart television, a smart watch, any IOT health monitoring device, or any combination thereof. In general, computing device 110 can be representative of any programmable mobile device and/or a combination of programmable mobile devices capable of executing machine-readable program instructions and communicating with users of other mobile devices via network 130 and/or capable of executing machine-readable program instructions and communicating with server computer 140. Additionally, computing device 110 can be, but is not limited to, any IOT wearable device that can measure, log, detect, record, and/or aggregate/collect a user's health data and/or vitals. User health data can be, but is not limited to, blood pressure, heart rate, respiratory rate, calories burned and/or calories consumed, pulse, oxygen levels, blood oxygen level, glucose level, blood pH level, salinity of user perspiration, skin temperature, galvanic skin response, electrocardiography (ECG or EKG) data, body temperature, any biometric data known in the art and/or any user health data known in the art.

In various embodiments, any occupants in a vehicle can be wearing an IOT health-monitoring smart device (e.g., computing device 110) that can emit, record, and/or monitor user health data. In various embodiments, when any occupant in a vehicle is wearing and/or is possession of computing device 110 and emergency tracking component 122 determines the user and/or wearer is having an "emergency," then the vehicle is automatically assigned a preferred parking space. In other embodiments, emergency tracking component 122 can automatically assign a preferred parking space at the nearest emergency facility. Additionally, in some embodiments, emergency tracking component 122 can provide turn by turn directions to the parking space. In various embodiments, emergency tracking component 122 can monitor the occupancy of preferred parking spaces and/or parking spaces by utilizing geofencing (e.g., geofenced smart parking). In some embodiments, emergency tracking component 122 can continually monitor preferred parking spaces and/or parking spaces. In various embodiments, in the event the assigned parking space is taken and/or occupied by a different vehicle before the user arrives emergency tracking component 122 can assign/reassign the closest and most convenient parking space, in which in some embodiments can be based on the user's current location. In some embodiments, emergency tracking component 122 can generate a list of priority park spots for the user to select and/or store until the user parks, just in case the spot is taken and/or occupied by another vehicle before the user arrives.

User interface (UI) 106 provides an interface to emergency tracking component 122 on server computer 120 for a user of mobile device 110. In one embodiment, UI 106 can be a graphical user interface (GUI) or a web user interface (WUI) and can display text, documents, web browser windows, user options, application interfaces, driving instructions, parking space information (e.g., parking space number), and/or instructions for operation, and include the information (such as graphic, text, and sound) that a program presents to a user and the control sequences the user employs to control the program. In another embodiment, UI 106 can also be mobile application software that provides an interface between a user of mobile device 110 and server computer 120. Mobile application software, or an "app," is a computer program designed to run on smart phones, tablet computers and other mobile devices. In an embodiment, UI 106 enables the user of mobile device 110 to send data, input data, edit data, correct data and/or receive data. In various embodiments, UI 106 can enable the user to upload/enter user health data, location data, and/or vehicle information to emergency tracking component 122 for analysis, cognitive learning, and/or parking space assignment. In various embodiments, UI 106 enables the user to communicate with emergency tracking component 122.

Server computer 120 can be a standalone computing device, a management server, a web server, a mobile computing device, or any other electronic device or computing system capable of receiving, sending, and processing data. In other embodiments, server computer 120 can represent a server computing system utilizing multiple computers as a server system, such as in a cloud computing environment. In another embodiment, server computer 120 can be a laptop computer, a tablet computer, a netbook computer, a personal computer (PC), a desktop computer, a personal digital assistant (PDA), a smart phone, or any other programmable electronic device capable of communicating with mobile device 110 and other computing devices (not shown) within distributed data processing environment 100 via network 130. In another embodiment, server computer 120 represents a computing system utilizing clustered computers and components (e.g., database server computers, application server computers, etc.) that act as a single pool of seamless resources when accessed within distributed data processing environment 100. Server computer 120 can include emergency tracking component 122 and shared storage 124. Server computer 120 can include internal and external hardware components, as depicted, and described in further detail with respect to FIG. 3.

Shared storage 124 and local storage 108 can be a data repository and/or a database that can be written to and/or read by one or a combination of emergency tracking component 122, server computer 120 and/or computing devices 110. In the depicted embodiment, shared storage 124 resides on server computer 120. In another embodiment, shared storage 124 can reside elsewhere within distributed data processing environment 100 provided coverage assessment program 110 has access to shared storage 124. A database is an organized collection of data. Shared storage 124 and/or local storage 108 can be implemented with any type of storage device capable of storing data and configuration files that can be accessed and utilized by server computer 120, such as a database server, a hard disk drive, or a flash memory. In other embodiments, shared storage 124 and/or local storage can be hard drives, memory cards, computer output to laser disc (cold storage), and/or any form of data storage known in the art. In various embodiments, biomarker identifier component 122 can store and/or retrieve data from shared storage 124 and/or local storage 108. For example, emergency tracking component 122 stores user health data and vehicle data (e.g., license plate number, make and model, car color, and/or any other form of vehicle identification known in the art) to shared storage 124 to be retrieved later and used as a reference and/or element of analysis.

In various embodiments, emergency tracking component 122 can enable a user and/or medical professional to set a predetermined threshold on a user's health data as a baseline for emergency tracking component 122 to determine if the user is experiencing an emergency. For example, if a user's heart rate falls below 40 beats per minute (BPM) and/or systolic blood pressure rises higher than 180.

A preferred parking space can be, but is not limited to, a handicap parking space, temporary/short term parking, a regular parking space, any reserved parking known in the art and/or any government regulated parking space known in the art. In various embodiments, preferred parking spaces can be labeled with digital signs that can change the designation of the spot based on the occupant of the space and/or emergency. For example, the preferred parking space normally displays as a handicap parking space; however, in the event of an emergency, emergency tracking component 122 can change the handicap signage to read "reserved emergency parking." Additionally, in some embodiments, emergency tracking component 122 can display the user's vehicle license plates on the digital display. A digital display can be, but is not limited to, a light emitting diode (LED) screen, a liquid crystal display (LCD) screen, a plasma screen, and/or any digital screen and/or monitor known in the art that can display images and/or texts. In some embodiments, a digital display can include a speaker system to emit sound.

In some embodiments, the digital display can be the parking label plaque itself, hanging above the parking space (e.g., preferred parking space), and/or any visible signage associated with a particular parking space/preferred parking space. In some embodiments, the emergency tracking component 122 can assign a preferred parking space number, wherein each preferred parking space is numbered and associate the user's license plate with the assigned parking space number. In other embodiments, a user can just take an opened preferred parking space, in which the geo-fenced smart parking space and the biometric device (e.g., computing device 110) communicate and exchange information and designated the open preferred parking space as the user's emergency parking. For example, the driver has a broken arm, drives into a hospitals parking structure, and parks in an open/available handicap parking space. In this particular example, emergency tracking component 122 enables the biometric device and the handicap parking space to communicate, in which the biometric device notifies the handicap parking space the user is having and emergency by sending the handicap parking space the user's biometric data (e.g., user health data) and/or licenses plate number, in which the handicap parking space will display the users license plate number and/or change the digital display from handicap parking to emergency parking.

In various embodiments, emergency tracking component 122 can communicate with a Biometric and Geo-fenced Smart Parking lot (e.g., geo-fenced smart parking system) and enable the Biometric and Geo-fenced Smart Parking lot to read the user's health information (e.g., user health data) of any and/or all vehicles within this geo-fenced area to begin analysis on each of the occupants wearing the IOT devices (e.g., computing device 110). A geo-fence and/or geo-fencing is a virtual perimeter for a real-world geographic area. A geo-fence could be dynamically generated—as in a radius around a store or point location, or a geo-fence can be a predefined set of boundaries, like school attendance zones or neighborhood boundaries. The use of a geo-fence is called geo-fencing, and one example of usage involves a location-aware device of a location-based service (LBS) and/or global positioning system (GPS) user entering or exiting a geo-fence. In this particular example, this activity could trigger an alert to the device's user as well as messaging to the geo-fence operator.

In various embodiments, a temporary emergency situation will be assessed and/or assigned when the biometric health information on the IOT device (e.g., computing device 110), via emergency tracking component 122, shows the levels to be outside the predetermined range, sensing the individual is in an emergency, crisis, or otherwise "handicapped" situation. In various embodiments, emergency tracking component 122 can communicate with the Biometric and Geo-fenced Smart Parking lot and determine which preferred parking spaces and/or most convenient parking spaces are available.

In some embodiments, emergency tracking component 122 can notify the Biometric and Geo-fenced Smart Parking lot that the user is having an emergency, in which the Biometric and Geo-fenced Smart Parking lot can assign one or more available preferred and/or normal parking spaces to emergency tracking component 122 display to the user. In various embodiments, emergency tracking component 122 can identify one or more available preferred and/or normal parking spaces, in which the identified one or more available preferred and/or normal parking spaces is ranked (e.g., a hierarchical list) based on the convenience and/or proximity to the entrance to the emergency facility (e.g., hospital and/or emergency room). In various embodiments, emergency tracking component 122 can display one or preferred and/or normal parking spaces to the user. In other embodiments, emergency tracking component 122 can display only the assigned preferred and/or normal parking space at a time. In various embodiments, the Biometric and Geo-fenced Smart Parking lot can consistently monitor the occupancy of preferred and/or normal parking spaces and if the Biometric and Geo-fenced Smart Parking lot determines that the identified and/or assigned parking space is taken before the user arrives the Biometric and Geo-fenced Smart Parking can notify emergency tracking component 122, in which emergency tracking component 122 can assign/reassign the user one or more additional available preferred and/or normal parking spaces. In various embodiments, emergency tracking component 122 assigns the user one or more of the identified parking spaces. In various embodiments, emergency tracking component 122 can determine and/or detect when a user's vehicle is occupying the assigned parking space, via geo-fenced smart parking (e.g., geofencing).

Figure 2:
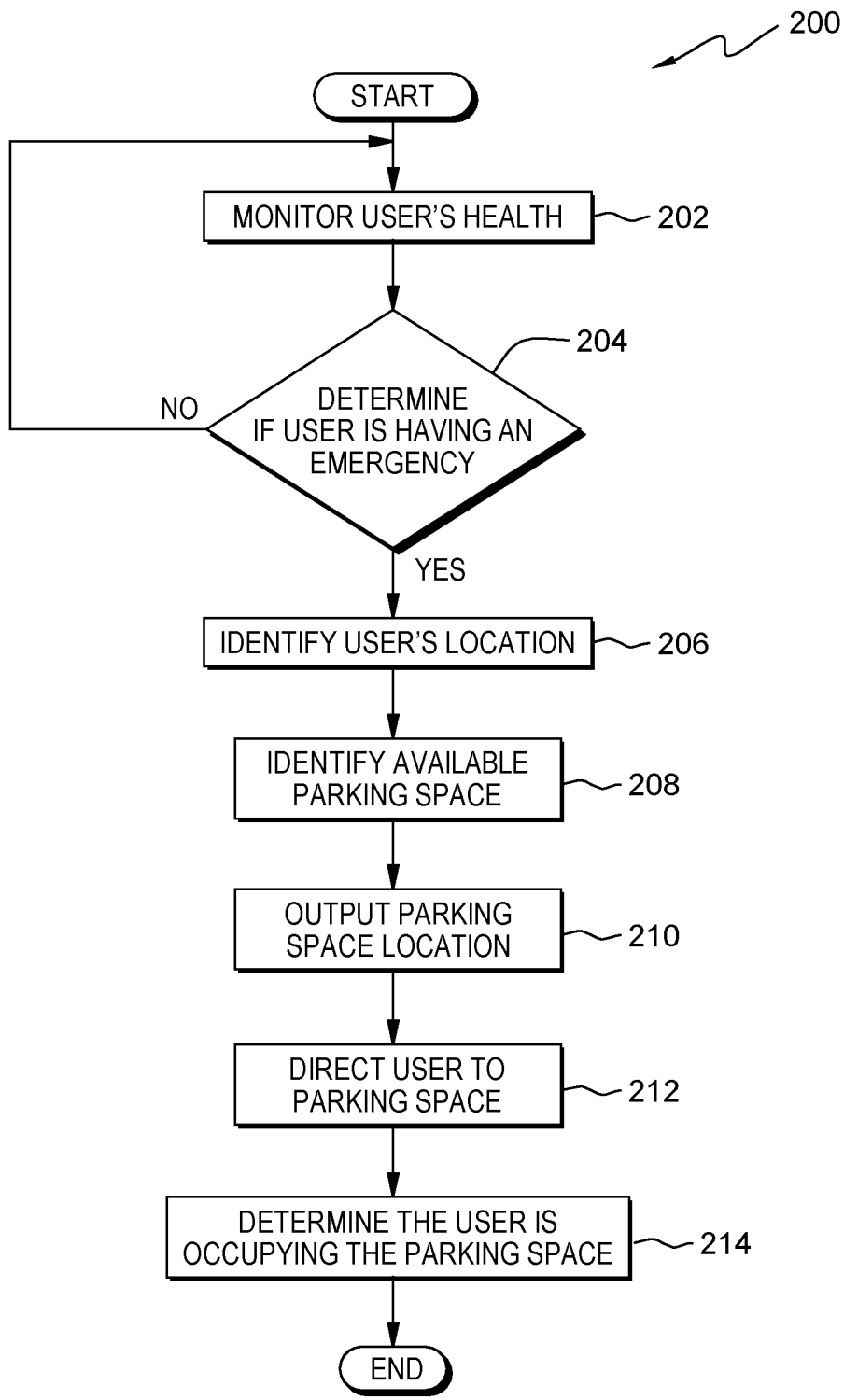
FIG. 2 is a flowchart depicting operational steps of emergency tracking component 122, on a server computer within the distributed data processing environment of FIG. 1, for filtering values returned to a client application, in accordance with an embodiment of the present invention.

FIG. 2 is a flowchart depiction operational steps of emergency tracking component 122, generally designated 200, on server computer 120 within distributed data processing environment 100 of FIG. 1, monitoring biometric and biomarker data, in accordance with an embodiment of the present invention. FIG. 2 provides only an illustration of one implementation and does not imply any limitations with regard to the environments in which different embodiments may be implemented. Many modifications to the depicted environment may be made by those skilled in the art without departing from the scope of the invention as recited by the claims.

In step 202, emergency tracking component 122 monitor's user health. In various embodiments, emergency tracking component 122 can monitor a user's health (e.g., user health data), via computing device 110 (e.g., biometric device). For example, a passenger in a vehicle is wearing an IOT health-monitoring smart device (e.g., computing device 110), in which the IOT health-monitoring smart device monitor's the passengers blood pressure, heart rate, respiratory rate, calories burned and/or calories consumed, pulse, oxygen levels, blood oxygen level, glucose level, blood pH level, salinity of user perspiration, skin temperature, galvanic skin response, electrocardiography (ECG or EKG) data, body temperature, any biometric data known in the art and/or any user health data known in the art. In some embodiments, emergency tracking component 122 can continuously monitor user health data and/or be programed to measure user health data in predetermined time intervals.

In step 204, emergency tracking component 122 determines if the user is having an emergency. In various embodiments, emergency tracking component 122 can determine if a user is having an emergency, such as: heart attack, pregnancy related emergency, intoxicated, broken bone, passing a kidney stone and/or experiencing any other health situation that raises their health-related biometrics (e.g., user health data) to a predetermined priority state (e.g., predetermined threshold). For example, a passenger in a vehicle is wearing an IOT health-monitoring smart device (e.g., computing device 110) and emergency tracking component 122 detects that the passengers blood pressure has risen to 185 (systolic) over 115 (diastolic), which is above the predetermined threshold. In another example, emergency tracking component 122 determines that a user's blood sugar level reads 190 milligrams of glucose per deciliter of blood (mg/dl), emergency tracking component 122 can alert the user, one or more medical professionals, one or more designated members (e.g., friends and/or family), and/or assign a preferred parking space. In various embodiments, if emergency tracking component 122 determines that a user is having an emergency then emergency tracking component 122 will advance to step 206 (Yes branch); however, if emergency tracking component 122 does not determine a user is an emergency then emergency tracking component 122 will repeat steps 202 through 204 (No branch). In various embodiments, emergency tracking component 122 can repeat steps 202-204 continuously until emergency tracking component 122 determines that the user is experiencing an emergency.

In step 206, emergency tracking component 122 can identify a user's location. In various embodiments, responsive to determining the user is having an emergency, emergency tracking component 122 can access a user's geographic location information from computing device 110. In various embodiments, emergency tracking component 122 can determine a user's location within a parking structure.

In step 208, emergency tracking component 122 can identify an available parking space. In various embodiments, emergency tracking component 122 can identify one or more available parking spaces, via geo-fenced smart parking. In various embodiments, emergency tracking component 122 can utilize both biometric and/or geo-fenced smart parking lot, in which an established geo-fenced area that includes the parking space, parking lot and/or parking structure itself as well as a predetermined area surrounding it to automatically sense the vehicle is within the geo-fenced area. For example, 500 feet outside the parameter of the parking lot and/or parking structure, the parking lot and/or parking structure itself, and/or individual parking spaces. In another example, emergency tracking component 122 can notify the Biometric and Geo-fenced Smart Parking lot that the user is having an emergency and requires a parking space from any distance. In various embodiments, a predetermined area can be set up on a case by case basis for each parking lot and/or parking structure which depends on the density of the population and surrounding buildings it is in, the location of the parking space and/or parking structure on the property, and/or number of parking spaces either regular or preferred parking.

In step 210, emergency tracking component 122 outputs a parking space location. In various embodiments, emergency tracking component 122 can output locations to one or more preferred and/or normal parking space a user. In various embodiments, emergency tracking component 122 can output a ranked list of available preferred and/or normal parking spaces. In some embodiments, the user can select one or more parking spaces from the outputted one or more preferred and/or normal parking spaces. In other embodiments, emergency tracking component 122 automatically assigns a parking space from the outputted one or more preferred and/or normal parking spaces. In various embodiments, when a user is assigned a parking space the license plate of the vehicle will be scanned and a particular parking spot can be assigned to the user's vehicle for the duration of that vehicle's parking needs. The license plate information will be displayed above and/or near the assigned parking space, via digital display, so that it will be evident to all that spot has been assigned to that particular vehicle. In various embodiments, emergency tracking component 122 can change the signage of the parking space to preferred, via digital display. In some embodiments, emergency tracking component 122 can notify the geo-fencing smart parking system the user is in the assigned parking space, in which the digital display can update the plague to new signage and/or display the user's license plate.

In step 212, emergency tracking component 122 directs a user to the parking space. In various embodiments, emergency tracking component 122 can direct a user to one or more assigned parking spaces. In various embodiments, emergency tracking component 122 can navigate the user to the parking structure and/or to the parking space in the parking structure.

In step 214, emergency tracking component 122 determines the user is occupying a parking space. In various embodiments, emergency tracking component 122 can determine that a user is occupying the assigned parking space by utilizing geofencing (e.g., geo-fenced smart parking) to detect the user's vehicle. For example, emergency tracking component 122 communicating with the geo-fenced smart parking system, in which emergency tracking component 122 notifies the user and the geo-fenced smart parking system that the user's vehicle is occupying the assigned parking space. In some embodiments, emergency tracking component 122 can determine that a user is occupying the one or more identified parking spaces and/or one or more outputted parking spaces. In this particular embodiment, when emergency tracking component 122 determines the user is occupying the assigned parking space, then emergency tracking component 122 can display the user's license plate on the assigned parking spots digital display and/or change the digital display on the assigned parking spot to a different symbol and/or marking.

Figure 3:
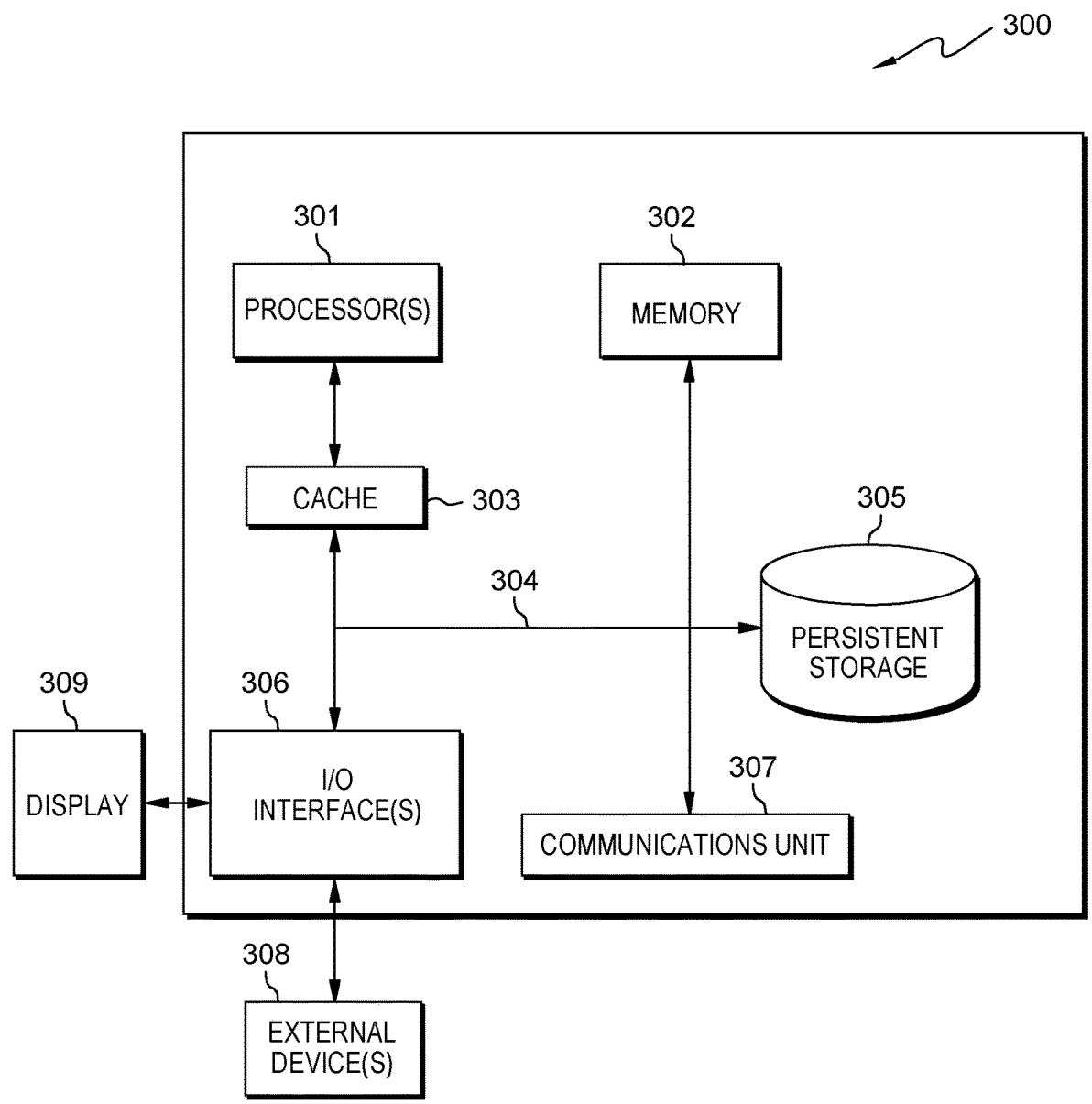
FIG. 3 depicts a block diagram of components of the server computer executing the intelligent mapping program within the distributed data processing environment of FIG. 1, in accordance with an embodiment of the present invention.

FIG. 3 depicts a block diagram of components of server computer 120 within distributed data processing environment 100 of FIG. 1, in accordance with an embodiment of the present invention. It should be appreciated that FIG. 3 provides only an illustration of one implementation and does not imply any limitations with regard to the environments in which different embodiments can be implemented. Many modifications to the depicted environment can be made.

FIG. 3 depicts computer system 300, where server computer 120 represents an example of computer system 300 that includes biomarker identifier component 122. The computer system includes processors 301, cache 303, memory 302, persistent storage 305, communications unit 307, input/output (I/O) interface(s) 306 and communications fabric 304. Communications fabric 304 provides communications between cache 303, memory 302, persistent storage 305, communications unit 307, and input/output (I/O) interface(s) 306. Communications fabric 304 can be implemented with any architecture designed for passing data and/or control information between processors (such as microprocessors, communications and network processors, etc.), system memory, peripheral devices, and any other hardware components within a system. For example, communications fabric 304 can be implemented with one or more buses or a crossbar switch.

Memory 302 and persistent storage 305 are computer readable storage media. In this embodiment, memory 302 includes random access memory (RAM). In general, memory 302 can include any suitable volatile or non-volatile computer readable storage media. Cache 303 is a fast memory that enhances the performance of processors 301 by holding recently accessed data, and data near recently accessed data, from memory 302.

Program instructions and data used to practice embodiments of the present invention may be stored in persistent storage 305 and in memory 302 for execution by one or more of the respective processors 301 via cache 303. In an embodiment, persistent storage 305 includes a magnetic hard disk drive. Alternatively, or in addition to a magnetic hard disk drive, persistent storage 305 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 305 may also be removable. For example, a removable hard drive may be used for persistent storage 305. Other examples include optical and magnetic disks, thumb drives, and smart cards that are inserted into a drive for transfer onto another computer readable storage medium that is also part of persistent storage 305.

Communications unit 307, in these examples, provides for communications with other data processing systems or devices. In these examples, communications unit 307 includes one or more network interface cards. Communications unit 307 may provide communications through the use of either or both physical and wireless communications links. Program instructions and data used to practice embodiments of the present invention may be downloaded to persistent storage 305 through communications unit 307.

I/O interface(s) 306 enables for input and output of data with other devices that may be connected to each computer system. For example, I/O interface 306 may provide a connection to external devices 308 such as a keyboard, keypad, a touch screen, and/or some other suitable input device. External devices 308 can also include portable computer readable storage media such as, for example, thumb drives, portable optical or magnetic disks, and memory cards. Software and data used to practice embodiments of the present invention can be stored on such portable computer readable storage media and can be loaded onto persistent storage 305 via I/O interface(s) 306. I/O interface(s) 306 also connect to display 309.

Display 309 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for detecting a health emergency and assigning preferred parking, the method comprising:
    collecting, by one or more computing devices, user health data;
    determining, by one or more processors, a user is having an emergency based on the user health data collected by the one or more computing devices and the user health data falling below or above a predetermined threshold set by a medical professional;
    identifying, by the one or more processors, a location of the user by accessing geographic location information of the user from the one or more computing devices;
    alerting, by the one or more processors, one or more medical professionals and one or more designated members of the determined emergency and the location of the user;
    identifying, by geo-fencing sensors and the one or more computing devices, one or more available parking spaces in a geo-fenced smart parking system based on the location of the user and proximity to an emergency facility, wherein the identifying one or more available parking spaces includes ranking the parking spaces in a hierarchical list based on respective proximity to an entrance of the emergency facility;
    assigning, by an emergency tracking component and the geo-fenced smart parking system, a preferred parking space to the user based on the identified one or more available parking spaces within the geo-fenced smart parking system, wherein the preferred parking space is an available parking space closest to the emergency facility, and wherein assigning a preferred parking space comprises:
        scanning a license plate of a vehicle associated with the user and assigning the vehicle associated with the user the preferred parking space;
    outputting, by the one or more processors, the preferred parking space within the geo-fenced smart parking system to the user; and
    storing, by the one or more processors, the user health data and vehicle data of the vehicle associated with the user in a database to be retrieved and used as a reference and element of analysis, wherein vehicle data comprises: license plate number, make and model of the vehicle, and car color.

2. The method of claim 1, further comprising:
    directing, by the one or more processors, the user to the outputted preferred parking space; and
    determining, by the one or more processors, the user is occupying the preferred parking space.

3. The method of claim 1, wherein the one or more available parking spaces comprise a digital display, wherein the digital display comprises a speaker system to emit sound.

4. The method of claim 3, wherein the digital display is updated to display new signage and display a license plate number of the vehicle.

5. The method of claim 1, wherein the identified one or more available parking spaces is consistently monitored, and wherein a parking spot is reassigned if the outputted parking space is taken before the user arrives.

6. The method of claim 1, wherein user data comprises: blood pressure, heart rate, respiratory rate, calories burned and calories consumed, pulse, oxygen levels, blood oxygen level, glucose level, blood pH level, salinity of user perspiration, skin temperature, galvanic skin response, electrocardiography data, and body temperature.

7. The method of claim 1, further comprising:
enabling, by the one or more processors, the one or more computing devices and geo-fenced smart parking system to communicate and exchange user data, user location data, and parking data;
enabling, by the one or more processors, the one or more computing devices and geo-fenced smart parking system to read the user health data of users within the geo-fenced smart parking system; and
analyzing, by the one or more processors, each user wearing the one or more computing devices.

8. A computer system for detecting a health emergency and assigning preferred parking, the computer system comprising:
one or more computer processors;
one or more computer readable storage devices;
program instructions stored on the one or more computer readable storage devices for execution by at least one of the one or more computer processors, the stored program instructions comprising:
program instructions to collect, by one or more computing devices, user health data;
program instructions to determine a user is having an emergency based on the user health data collected by the one or more computing devices and the user health data falling below or above a predetermined threshold set by a medical professional;
program instructions to identify a location of the user by accessing geographic location information of the user from the one or more computing devices;
program instructions to alert one or more medical professionals and one or more designated members of the determined emergency and the location of the user;
program instructions to identify, by geo-fencing sensors and the one or more computing devices, one or more available parking spaces in a geo-fenced smart parking system based on the location of the user and proximity to an emergency facility, wherein the identifying one or more available parking spaces includes ranking the parking spaces in a hierarchical list based on respective proximity to an entrance of the emergency facility;
program instructions to assign, by an emergency tracking component and the geo-fenced smart parking system, a preferred parking space to the user based on the identified one or more available parking spaces within the geo-fenced smart parking system, wherein the preferred parking space is an available parking space closest to the emergency facility, and wherein assigning a preferred parking space comprises:
program instructions to scan a license plate of a vehicle associated with the user and assigning the vehicle associated with the user the preferred parking space;
program instructions to output the preferred parking space within the geo-fenced smart parking system to the user; and
program instructions to store the user health data and vehicle data of the vehicle associated with the user in a database to be retrieved and used as a reference and element of analysis, wherein vehicle data comprises: license plate number, make and model of the vehicle, and car color.

9. The computer system of claim 8, further comprising:
program instructions to direct the user to the outputted preferred parking space; and
program instructions to determine the user is occupying the preferred parking space.

10. The computer system of claim 8, wherein the one or more available parking spaces comprise a digital display, wherein the digital display comprises a speaker system to emit sound.

11. The computer system of claim 10, wherein the digital display is updated to display new signage and display a license plate number of the vehicle.

12. The computer system of claim 8, wherein the identified one or more available parking spaces is consistently monitored, and wherein a parking spot is reassigned if the outputted parking space is taken before the user arrives.

13. The computer system of claim 8, wherein user data comprises: blood pressure, heart rate, respiratory rate, calories burned and calories consumed, pulse, oxygen levels, blood oxygen level, glucose level, blood pH level, salinity of user perspiration, skin temperature, galvanic skin response, electrocardiography data, and body temperature.

14. The computer system of claim 8, further comprising:
program instructions to enable the one or more computing devices and geo-fenced smart parking system to communicate and exchange user data, user location data, and parking data;
program instructions to enable the one or more computing devices and geo-fenced smart parking system to read the user health data of users within the geo-fenced smart parking system; and
program instructions to each user wearing the one or more computing devices.

15. A computer program product for detecting a health emergency and assigning preferred parking, the computer program product comprising:
one or more computer readable storage devices and program instructions stored on the one or more computer readable storage devices, the stored program instructions comprising:
program instructions to collect, by one or more computing devices, user health data;
program instructions to determine a user is having an emergency based on the user health data collected by the one or more computing devices and the user health data falling below or above a predetermined threshold set by a medical professional;
program instructions to identify a location of the user by accessing geographic location information of the user from the one or more computing devices;
program instructions to alert one or more medical professionals and one or more designated members of the determined emergency and the location of the user;
program instructions to identify, by geo-fencing sensors and the one or more computing devices, one or more available parking spaces in a geo-fenced smart parking system based on the location of the user and proximity to an emergency facility, wherein the identifying one or more available parking spaces includes ranking the parking spaces in a hierarchical list based on respective proximity to an entrance of the emergency facility;
program instructions to assign, by an emergency tracking component and the geo-fenced smart parking system, a preferred parking space to the user based on the identified one or more available parking spaces within the geo-fenced smart parking system, wherein the preferred parking space is an available parking space closest to the emergency facility, and wherein assigning a preferred parking space comprises:
  program instructions to scan a license plate of a vehicle associated with the user and assigning the vehicle associated with the user the preferred parking space;
  program instructions to output the preferred parking space within the geo-fenced smart parking system to the user; and
  program instructions to store the user health data and vehicle data of the vehicle associated with the user in a database to be retrieved and used as a reference and element of analysis, wherein vehicle data comprises: license plate number, make and model of the vehicle, and car color.

16. The computer program product of claim 15, further comprising:
  program instructions to direct the user to the outputted preferred parking space; and
  program instructions to determine the user is occupying the preferred parking space.

17. The computer program product of claim 15, wherein the one or more available parking spaces comprise a digital display, wherein the digital display comprises a speaker system to emit sound, and wherein the digital display is updated to display new signage and display a license plate number of the vehicle.

18. The computer program product of claim 15, wherein the identified one or more available parking spaces is consistently monitored, and wherein a parking spot is reassigned if the outputted parking space is taken before the user arrives.

19. The computer program product of claim 15, wherein user data comprises: blood pressure, heart rate, respiratory rate, calories burned and calories consumed, pulse, oxygen levels, blood oxygen level, glucose level, blood pH level, salinity of user perspiration, skin temperature, galvanic skin response, electrocardiography data, and body temperature.

20. The computer program product of claim 15, further comprising:
  program instructions to enable the one or more computing devices and geo-fenced smart parking system to communicate and exchange user data, user location data, and parking data;
  program instructions to enable the one or more computing devices and geo-fenced smart parking system to read the user health data of users within the geo-fenced smart parking system; and
  program instructions to each user wearing the one or more computing devices.

* * * * *